(12) United States Patent
Okada et al.

(10) Patent No.: US 7,985,706 B2
(45) Date of Patent: Jul. 26, 2011

(54) UNIFORMLY, HIGHLY DISPERSED METAL CATALYST AND PROCESS FOR PRODUCING THE SAME

(75) Inventors: Yoshimi Okada, Kanagawa (JP); Toshiji Makabe, Kanagawa (JP); Masashi Saito, Kanagawa (JP); Takako Nishijima, Kanagawa (JP)

(73) Assignee: Chiyoda Corporation, Yokohama-shi (JP)

( * ) Notice: Subject to any disclaimer, the term of this patent is extended or adjusted under 35 U.S.C. 154(b) by 676 days.

(21) Appl. No.: 11/922,462

(22) PCT Filed: Jun. 19, 2006

(86) PCT No.: PCT/JP2006/312237
§ 371 (c)(1),
(2), (4) Date: Dec. 19, 2007

(87) PCT Pub. No.: WO2006/137358
PCT Pub. Date: Dec. 28, 2006

(65) Prior Publication Data
US 2009/0105511 A1 Apr. 23, 2009

(30) Foreign Application Priority Data

Jun. 20, 2005 (JP) ................. 2005-178804

(51) Int. Cl.
| | | |
|---|---|---|
| B01J 27/02 | (2006.01) | |
| B01J 27/053 | (2006.01) | |
| B01J 27/055 | (2006.01) | |
| B01J 27/049 | (2006.01) | |
| B01J 27/043 | (2006.01) | |
| B01J 27/045 | (2006.01) | |
| B01J 23/00 | (2006.01) | |
| B01J 23/40 | (2006.01) | |
| B01J 23/42 | (2006.01) | |
| B01J 23/60 | (2006.01) | |
| B01J 23/72 | (2006.01) | |
| C07C 4/02 | (2006.01) | |
| C07C 5/00 | (2006.01) | |
| C07C 5/09 | (2006.01) | |
| C07C 5/327 | (2006.01) | |
| C07C 5/373 | (2006.01) | |

(52) U.S. Cl. ........ 502/216; 502/217; 502/218; 502/221; 502/222; 502/223; 502/325; 502/326; 502/329; 502/331; 585/440; 585/616; 585/654

(58) Field of Classification Search .......... 502/216–218, 502/221–223, 325, 326, 329, 331; 585/440, 585/616, 654
See application file for complete search history.

(56) References Cited

U.S. PATENT DOCUMENTS 4,119,568 A  10/1978 Nishida et al.
4,123,391 A * 10/1978 Noguchi et al. ............... 502/207

FOREIGN PATENT DOCUMENTS

JP      51-77593 A      7/1976
(Continued)

OTHER PUBLICATIONS

14th "Catalysis School Text" (2003), pp. 35-44, organized by Kanto Branch Commission, Catalysis Society of Japan.

(Continued)

*Primary Examiner* — Patricia L Hailey
(74) *Attorney, Agent, or Firm* — Birch, Stewart, Kolasch & Birch, LLP

(57) ABSTRACT

Provided are: a uniformly, highly dispersed metal catalyst including a catalyst carrier and a catalyst metal being loaded thereon dispersed throughout the carrier, the uniformly, highly dispersed metal catalyst having excellent performances with respect to catalytic activity, selectivity, life, etc.; and a method of producing the same. The uniformly, highly dispersed metal catalyst includes a catalyst carrier made of a metal oxide and a catalyst metal having catalytic activity, the catalyst metal being loaded on the catalyst carrier, in which the catalyst carrier is a sulfur-containing catalyst carrier having sulfur or a sulfur compound almost evenly distributed throughout the carrier and the catalyst metal is loaded on the sulfur-containing catalyst carrier in a substantially evenly dispersed manner over the entire carrier substantially according to the distribution of the sulfur or the sulfur compound.

12 Claims, 10 Drawing Sheets

EGG SHELL TYPE   UNIFORM TYPE

METAL SUPPORTED PORTION

FOREIGN PATENT DOCUMENTS

| | | | |
|---|---|---|---|
| JP | 5-200296 | A | 8/1993 |
| JP | 2001-70794 | A | 3/2001 |
| JP | 2001-179105 | A | 7/2001 |
| JP | 2001-353444 | * | 12/2001 |
| JP | 2001-353444 | A | 12/2001 |

OTHER PUBLICATIONS

15th "Catalysis School Text" (2004), pp. 35-44, organized by Kanto Branch Commission, Catalysis Society of Japan.

Catalyst Design, vol. 5, pp. 134-141, 1985, Catalyst Lecture edited by Catalysis Society of Japan.

* cited by examiner

A: Rh SUPPORTED STATE IN THE ABSENCE OF SULFUR

B: Rh SUPPORTED STATE IN THE PRESENCE OF SULFUR

US 7,985,706 B2

UNIFORMLY, HIGHLY DISPERSED METAL CATALYST AND PROCESS FOR PRODUCING THE SAME

TECHNICAL FIELD

The present invention relates to a metal loaded catalyst for use in manufacturing chemical products, producing hydrogen, cleaning the environment, such as cleaning exhaust gas, etc. More especially, the present invention relates to a uniformly, highly dispersed metal loaded catalyst in which sulfur or a sulfur compound are substantially uniformly dispersed throughout the cross section of a catalyst carrier and catalyst metal is loaded on the carrier in a state where the catalyst metals are substantially uniformly dispersed throughout the cross section of the carrier almost substantially in agreement with the distribution of the sulfur or sulfur compound, a method of using the same, and a sulfur-containing porous metal oxide for use in producing the same.

BACKGROUND ART

A metal loaded catalyst in which various catalytic metal species are loaded on a catalyst carrier made of a metal oxide is used in an extremely wide range of fields, for example, not only dehydrogenation reaction in which hydrogenated aromatics such as methylcyclohexane, cyclohexane, and decalin are dehydrogenated into the corresponding aromatics and hydrogen but also manufacturing of chemical products and fuels by dehydrogenation reaction of various compounds, hydrogenation reaction which is a reverse reaction of the dehydrogenation reaction and reforming reaction; and environmental clean-up such as cleaning automobile exhaust gas, and the like.

Generally, such metal loaded catalysts are manufactured as follows: a porous catalyst carrier made of a metal oxide such as alumina or silica etc., is prepared; when platinum is loaded on the obtained porous catalyst carrier, the obtained porous catalyst carrier is impregnated with a solution of a catalyst metal compound, such as a chloroplatinic acid aqueous solution, a platinum ammonium chloride aqueous solution, and a solution of an organoplatinum compound such as platinum acetylacetonate; the resultant is dried to form a dried matter loading the catalyst metal compound; the dried matter is calcined, e.g., at 350 to 800ยฐ C. for 0.5 to 24 hours to form a calcined matter loading the catalyst metal compound; and, as required, the obtained calcined matter loading the catalyst metal compound is subjected to hydrogen reduction, e.g., at 250 to 800ยฐ C. for 0.5 to 24 hours.

However, the metal loaded catalyst manufactured by such a procedure has the following problems. For example, when a platinum-loaded alumina catalyst in which platinum, being one of typical active metal species as catalyst metal, is loaded on an alumina carrier, being used most widely as a catalyst carrier, is taken as an example, it is known that since the adsorbability of a platinum compound to the alumina carrier is high, the platinum compound is adsorbed and fixed as it is to the outer shell part of the alumina carrier before the platinum compound is dispersed inside the alumina carrier, which forms a so-called egg shell-type metal loaded catalyst, as viewed in the cross section, the catalyst metal being loaded only on the outer shell part and no catalytic metal species being loaded inside the carrier (see 14th "Catalysis School Text" (2003), pages 35 to 44 and 15th "Catalysis School Text" (2004), pages 35 to 44, organized by Kanto Branch Commission, Catalysis Society of Japan).

In the case of the reaction in which the dispersion resistance is high inside a catalyst, the reaction occurs preferentially in the outer shell of the catalyst. Thus, the egg shell-type catalyst is advantageous in such a reaction. However, when a certain amount of active metal is to be loaded only on the outer shell of the catalyst particles, the density of the active metal particles increase, which presumably leads to possibilities that the active metal particles can not be sufficiently dispersed, catalyst deactivation due to sintering or coking is likely to occur, etc. Therefore, in a reaction which is not influenced by the dispersion resistance, it is presumably advantageous to design a catalyst in such a manner as to reduce the influences by fully utilizing the surface area of a carrier.

However, it is not easy that the active metal such as platinum is uniformly dispersed as far as the inside of catalyst carrier particles, and a method using a competitive adsorption agent having high adsorbability to a carrier has been used heretofore (Catalyst Design, volume 5, pages 134 to 141, Catalyst Lecture edited by Catalysis Society of Japan). However, also in the method, it is relatively difficult to prepare a catalyst in which the active metal is uniformly dispersed thoroughly, and there is a possibility that the concentration gradient of loaded metal appears toward the center of the catalyst particles.

Non-patent Document 1: 14th "Catalysis School Text" (2003), pages 35 to 44, organized by Kanto Branch Commission, Catalysis Society of Japan Non-patent Document 2: 15th "Catalysis School Text" (2004), pages 35 to 44, organized by Kanto Branch Commission, Catalysis Society of Japan Non-patent Document 3: Catalyst Design, volume 5, pages 134 to 141, Catalyst Lecture edited by Catalysis Society of Japan

DISCLOSURE OF THE INVENTION

Problem to be Solved by the Invention

The inventors of the present invention carried out extensive research on loading catalyst metal such as platinum on a catalyst carrier such as alumina or silica in a state where the catalyst metal is uniformly dispersed as far as the inside of the catalyst carrier by an impregnation method. As a result, it is unexpectedly found that, by substantially uniformly dispersing sulfur or a sulfur compound throughout the cross section of the catalyst carrier beforehand, catalyst metal is loaded substantially in agreement with the distribution of the sulfur or sulfur compound, thereby easily obtaining a uniformly, highly dispersed metal loaded catalyst in which the catalytic metal is substantially uniformly dispersed and loaded over the entire cross section of the catalyst carrier, and thus the present invention has been accomplished.

Accordingly, the present invention aims to provide a uniformly, highly dispersed metal catalyst in which the catalytic metal is loaded on the catalyst carrier in a state where the catalytic metal is substantially uniformly dispersed throughout the cross section of the catalyst carrier and which has excellent performances in terms of catalytic activity, selectivity, life, etc.

The present invention also aims to provide a method of producing such a uniformly, highly dispersed metal catalyst which has excellent performances in terms of catalytic activity, selectivity, life, etc., a method of using the same, and a sulfur-containing porous metal oxide for use in the method of producing the same.

Means for Solving the Problems

The present invention provides a uniformly, highly dispersed metal catalyst including: a catalyst carrier made of a metal oxide; and a catalyst metal having catalytic activity, the catalyst metal being loaded on the catalyst carrier, in which: the catalyst carrier is a sulfur-containing catalyst carrier containing sulfur or a sulfur compound which is dispersed throughout across section of the carrier; and in the sulfur-containing catalyst carrier, the catalyst metal is dispersed and loaded over an entire cross section of the catalyst carrier substantially in agreement with distribution of the sulfur or the sulfur compound.

In addition, the present invention provides a method of producing a uniformly, highly dispersed metal catalyst including: preparing a sulfur-containing catalyst carrier in which sulfur or a sulfur compound is dispersed throughout a cross section thereof; impregnating the obtained sulfur-containing catalyst carrier with an aqueous solution of catalyst metal compound and drying the resulting catalyst carrier to obtain a dried matter loading the catalyst metal compound; reducing the dried matter loading the catalyst metal compound as it is in a hydrogen atmosphere or calcining the dried matter loading the catalyst metal compound to obtain a calcined matter loading catalyst metal; and reducing the obtained calcined matter loading the catalyst metal with hydrogen.

In this specification, the wording "uniform-type" used in the uniformly dispersed metal catalyst of the present invention refers to a state where catalyst metal particles are substantially uniformly loaded over the entire cross section of the catalyst carrier, and the wording "highly dispersed" refers to a state where the particle diameter of the loaded metal is sufficiently small and the particle is dispersed to a high degree. More specifically, the uniformly, highly dispersed metal catalyst of the present invention refers to a uniformly, highly dispersed metal catalyst in which: the numerical value of a metal dispersion degree, which will be mentioned later, is high; and the metal particles are substantially uniformly loaded over the entire cross section of the catalyst carrier while a high dispersion state, in which the particle diameter of the loaded metal is sufficiently small, is maintained.

Examples of the metal oxides used for a catalyst carrier in the present invention include metal oxides containing one or two or more metals selected from aluminum (Al), silicon (Si), zirconium (Zi), magnesium (Mg), calcium (Ca), titanium (Ti), vanadium (Va), chromium (Cr), manganese (Mn), iron, (Fe), cobalt (Co), nickel (Ni), copper (Cu), zinc (Zn), gallium (Ga), yttrium (Y), niobium (Nb), molybdenum (Mo), tungsten (W), lanthanum (La), and cerium (Ce). Alumina, silica, titania, zirconia, ceria, and the like are preferred.

When the above-mentioned catalyst carrier is alumina, a porous γ-alumina carrier is preferable as disclosed in JP 06-72005 B, for example. The porous γ-alumina carrier is obtained by washing by filtration a slurry of aluminum hydroxide generated by neutralizing aluminum salt, dehydrating and drying the obtained alumina hydrogel, and then calcining the resultant at 400 to 800° C. for about 1 to 6 hours. More preferable is a porous γ-alumina carrier obtained through a pH swing process in which the pH of alumina hydrogel is alternately fluctuated between a pH range of the dissolution of alumina hydrogel and a pH range of the precipitation of boehmite gel and simultaneously an alumina hydrogel forming substance is added for growing crystals of the alumina hydrogel when the pH is fluctuated from at least either one of the pH ranges to the other one of the pH ranges. The porous γ-alumina carrier obtained through the pH swing process is excellent in the uniformity of pore distribution, and excellent in that the physical properties of each pellet are stable because there is less variation in the physical properties also in the alumina carrier pellet after the formation of the carrier.

There is no limitation on the sulfur or sulfur compound to be dispersed in such a catalyst carrier beforehand for incorporation thereof insofar as the sulfur or sulfur compound has a sulfur element and can be uniformly dispersed in the catalyst carrier during the preparation of the catalyst carrier or after the preparation of the catalyst carrier. For example, sulfur crystal powders, and sulfur-containing compounds such as sulfuric acid, sulfate including ammonium sulfate can be mentioned. From the viewpoint that sulfur is likely to disperse on a carrier, sulfur compounds having solubility in water or an organic solvent are preferable, and sulfuric acid, ammonium sulfate, etc., can be mentioned as such sulfur compounds.

The amount of sulfur to be contained in a carrier is preferably 0.15% by weight or more and 5% by weight or less, and more preferably 0.15% by weight or more and 3% by weight or less. When the sulfur content is less than 0.15% by weight, the degree that metal is uniformly loaded as far as the center of the catalyst is low, while when the sulfur content exceeds 5% by weight, a problem is likely to occur that sulfur is likely to locally agglomerate and metal is not dispersed and loaded on such a portion. In view of the above, the most suitable sulfur content range is preferably 0.15 to 3.0% by weight considering the effect that metal is uniformly dispersed and loaded.

In the present invention, with respect to a method of preparing a sulfur-containing catalyst carrier containing the above-mentioned sulfur or sulfur compound, usable is a method capable of incorporating the sulfur or sulfur compound in a state where the sulfur or sulfur compound is uniformly dispersed throughout the cross section of the carrier. For example, the following methods are mentioned: method A involving kneading sulfur powder in a metal hydroxide gel serving as a precursor of a metal oxide obtained when preparing a catalyst carrier, forming the resultant into a predetermined shape, and drying and calcining the resultant; method B involving preparing a metal hydroxide gel serving as a precursor of a metal oxide containing sulfur using metal sulfate and/or sulfuric acid when preparing a catalyst carrier, forming the resultant into a predetermined shape, and drying and calcining the resultant; method C involving forming a metal hydroxide gel serving as a precursor of a metal oxide into a predetermined shape when preparing a catalyst carrier, drying the resultant to form a dry metal hydroxide gel, impregnating the dry metal oxide with a sulfur compound solution, and calcining the same; method D involving forming a metal hydroxide gel serving as a precursor of a metal oxide into a predetermined shape when preparing a catalyst carrier, drying the resultant to form a dry metal hydroxide, impregnating the dry metal hydroxide with a sulfur compound solution, and calcining the same; and method E involving forming a metal hydroxide gel serving as a precursor of a metal oxide into a predetermined shape, drying the resultant to form a dry metal hydroxide gel, calcining the dry metal hydroxide gel to form a calcined metal oxide, impregnating the calcined metal oxide with a sulfur compound solution such as an sulfuric acid aqueous solution and an ammonium sulfate solution, and further calcining the resultant.

With respect to calcining conditions when preparing the sulfur-containing catalyst carrier, the calcining temperature is usually 100° C. or higher and 1,000° C. or lower, and preferably 350° C. or higher and 800° C. or lower, and the calcining time is 0.5 hour or more and 48 hours or less, and preferably 1 hour or more and 24 hours or less. When the calcining temperature is lower than 350° C., conversion to an oxide from a hydroxide may not be fully performed, while when the calcining temperature is higher than 800° C., the surface area after calcining may be dramatically reduced.

In the present invention, there is no limitation on the catalyst metal to be loaded on the sulfur-containing catalyst carrier, and preferable is one or two or more metals selected from platinum (Pt), palladium (Pd), iridium (Ir), rhodium (Rh), ruthenium (Ru), nickel (Ni), copper (Cu), and zinc (Zn), and more preferably is platinum. When the catalyst carrier is, for example, the above-mentioned porous γ-alumina carrier and the catalyst metal is platinum, the loading amount of catalyst metal is 0.05% by weight or more and 5.0% or less, and preferably 0.1% by weight or more and 3.0% by weight or less. When the loading amount of platinum is less than 0.05% by weight, there is a problem that the activity is low, while when the loading amount of platinum exceeds 5.0% by weight, there are problems that the particle diameter of platinum increases, the selectivity is reduced, sintering is likely to occur, resulting in that deactivation is likely to occur.

The catalyst prepared as mentioned above may be formed into a general pellet in the forming process, or can also be fixed on a support in various forms such as a honeycomb and plate. In other words, the catalyst may be fixed on a support in the preparation processes of the sulfur-containing catalyst carrier described above or catalyst powder after loading catalyst metal may be fixed thereon. The sulfur-containing catalyst carrier or the catalyst to such a support can be fixed by a binder, calcining, or sintering, which are generally used for fixing an oxide catalyst to a honeycomb, a plate, etc.

In the present invention, it can be confirmed as to whether the catalyst metal s uniform, and in other words, the catalyst metal is substantially uniformly dispersed throughout the cross section of the carrier by observing quantitatively the concentration distribution of catalyst metal elements on the catalyst cross section by EPMA (Electron probe micro analyzer). According to the EPMA, fluorescence X rays, which are peculiar to elements and generated by irradiating a sample with electron beams, are detected, and the concentration of a specific element of the electron-beam-irradiation part is quantified from the detected intensity. Usually, the following analyses are possible: the surface analysis in which electron beams are emitted while shifting target irradiation portions, and the distribution states of specific elements throughout the sample cross section are indicated in different colors according to the detected intensity, whereby the distribution state thereof throughout the cross section is shown; and the line analysis which shows, in a graph, the detected intensity at the measurement position linearly traversing the sample cross section as a relative value.

In the cross section of the egg shell-type catalyst, catalyst metal is detected only in the outer shell of the cross section. The detected intensity in the measurement position inside the outer shell is notably small, and the catalyst metal concentration of the center is about ½ or less compared with that of the outer shell part. In contrast, in the uniformly, highly dispersed metal catalyst of the present invention, metal is loaded with high concentration as far as the center of the carrier cross section as well as the outer shell part of the carrier cross section. The metal concentration of the center with respect to the outer shell part, the catalyst metal can be uniformly dispersed from the outer shell part to the center of the cross section of the carrier within the range of preferably ±50%, more preferably ±30%, and still more preferably ±15% in terms of the detected intensity.

Moreover, it can be quantitatively captured as to whether the catalyst metal is highly dispersed, and in other words, the metal particle diameter is sufficiently small and the metal particles are highly dispersed, by the dispersion ratio (%) of the metal particles determined by a CO pulse adsorption method mentioned below. Here, the metal dispersion ratio is defined by the ratio of the number of metal atoms which are present on the outer face of the loaded metal particles with respect to a total number of the loaded metal atoms. For example, when metal particles containing 100 atoms are loaded, and 40 metal atoms out of the 100 atoms are present on the outer surface, the metal dispersion ratio is 40%. The metal dispersion ratio is usually measured by the CO pulse adsorption method, and the measurement is carried out by a method of determining the number of CO molecules adsorbing metal atoms which are present on the outer surface. When the forms of the metal particles are assumed to have a form of a cube or a regular octahedron, the metal particle diameter based on the assumption can be estimated from the result.

That is, the dispersion ratio of the catalyst metal of the present invention is 40% or higher, and preferably 60% or higher and 80% or lower. The average metal particle size equivalent to the dispersion ratio of 60% or higher is 10 Å or smaller, and the average metal particle size equivalent to the dispersion ratio of 70% is about 7 Å. The significances of increasing the metal dispersion ratio for reducing the size of the loaded metal particles as described above mainly reside in the following two respects. It is primarily mentioned that as the dispersion ratio of metal increases, the proportion of atoms which are present on the outer surface of metal particles increases, whereby the surface area of active metal increases, and the activity is improved. Second, in a cluster of small noble metal particles, since the number of platinum atoms forming a flat portion is small, flat adsorption of components such as a reaction raw material on metal is presumably difficult to achieve. For example, when hydrogenated aromatics are dehydrogenated using a platinum-loaded alumina catalyst in which platinum is highly dispersed as high as 10 Å or smaller, the flat portions of the noble metal surface to which aromatic molecules are adsorbed flat are presumably extremely small in view of the molecule size. Therefore, it is presumed that decomposition reactions can be inhibited because it is extremely rare that two or more carbon atoms of aromatics adsorb on the noble metal surface.

When platinum is taken as an example, the particle size of a commonly commercially-available platinum-loaded alumina catalyst is about 20 to 30 Å and the metal dispersion ratio is about 20 to 40% in many cases. It is said that it is relatively difficult to load platinum in a dispersion ratio as high as 20 Å or smaller. A highly dispersed catalyst with a dispersion ratio of 10 Å or smaller has been demanded not only from the viewpoint of increasing catalyst activity but also from the viewpoint of effectively using platinum resources. However, a catalyst having such a high dispersion ratio has not yet been prepared.

In the present invention, a porous metal oxide in which sulfur or a sulfur compound is contained preferably has the pore size controlled as uniformly as possible so that the pore distribution becomes sharp. Specifically, preferable is a porous metal oxide in which a sulfur-containing porous metal oxide has a surface area of 150 m$^2$/g or larger, a pore volume of 0.4 cm$^3$/g or larger, an average pore diameter of 40 to 300 Å, and the proportion of pores having an average pore diameter of 30 Å is 60% or higher with respect to a total pore volume. When the pore sizes of the porous metal oxide are made around the same size, the pore size distribution of the porous metal oxide is sharply controlled. Such a porous metal oxide is advantageous in a process of dispersing and loading sulfur and a process of dispersing and loading metal thoroughly in agreement with the distribution of sulfur.

When noble metal such as platinum and palladium is impregnated and loaded in an alumina carrier, the dispersion ratio of the noble metal after calcining varies depending on the pH value of an aqueous impregnation solution. In the present invention, the optimal range of the pH value is 1.0 to 5.0, and preferably 1.8 to 3.0. When the pH value of an impregnation solution is lower than 1.0, the dispersion ratio of noble metal after loading is low, and when the pH value is higher than 5.0, the dispersion ratio decreases. It is presumed that the decrease in dispersion ratio is caused by that the adsorbability of metal compound molecules to the alumina carrier is different depending on pH values upon impregnating and pH values largely affect particles growth by sintering at the time of calcining.

As a consequence of making the sizes of pores the almost same as described above, when a porous metal oxide whose pore distribution is sharply controlled is used for a carrier, the dispersion ratio of metal becomes higher compared with the case where a metal oxide whose pores are not controlled is used for a carrier. The dispersion ratio is further improved by adjusting the pH value of an aqueous solution for impregnating platinum to the optimal value. However, the platinum-loaded alumina catalyst thus prepared forms an egg shell-type catalyst in which platinum is loaded only on the shell part of the cross section. For example, when platinum is loaded using alumina, an egg shell-type platinum-loaded alumina catalyst prepared by using a porous γ-alumina whose pore distribution is sharply adjusted for a carrier, and impregnating the carrier with an aqueous impregnation solution whose pH value is adjusted to the optimal value has a dispersion ratio of platinum as high as 60 to 80%, even if sulfur or a sulfur compound is not present as in the present invention. However, since the acid site of alumina may remain inside the catalyst, treatment such as masking the remaining acid site with alkali metal is necessary for applying the catalyst to a reaction for highly inhibiting a decomposition reaction and the like.

The present invention makes it possible, for the first time, to prepare a uniformly, highly dispersed platinum-loaded alumina catalyst in which platinum is loaded over the entire cross section of the catalyst while maintaining the dispersion ratio as high as 60 to 80% by using an alumina carrier whose pore distribution is controlled and an aqueous platinum solution whose pH value is optimized, and dispersing sulfur or a sulfur compound throughout the cross section of the alumina carrier whose pore distribution is controlled. As described above, the significance of being uniform presumably resides in that a uniform catalyst is suitable for a system in which imparting dispersion resistance to the inside of the catalyst is suitable for a reaction, and in that since metal particles are dispersed throughout the inside of the carrier, there are distances between the metal particles, whereby the metal particles are difficult to agglomerate by sintering and the activity is less likely to deactivate by sintering.

Generally, in a reforming catalyst or dehydrogenation catalyst, particles of a noble metal such as platinum are bimetallized with a second metal components such as rhenium or tin to break the continuous arrangement of platinum atoms or the like, thereby suppressing the unnecessary adsorption of the carbon atoms of a raw material or a product and inhibiting a decomposition reaction. However, because, in the catalyst system of the present invention, noble metal particles are highly dispersed and the particle diameter is sufficiently small, the decomposition reaction occurring on platinum particles can presumably be inhibited without bimetallization.

However, when using a catalyst with alumina as a carrier, merely inhibiting the decomposition reaction that occurs on the platinum particles is not enough, and it is also necessary to inhibit the decomposition reaction that occurs on the acid sites of the alumina. Therefore, in many cases, the decomposition reaction occurring on the alumina surface is inhibited by masking these acid sites using alkali metals such as potassium and lithium. However, it is revealed that, in the catalyst using the alumina carrier containing sulfur or a sulfur compound of the present invention, even when the acid site is not masked with alkali metal, the decomposition reaction inhibitory effect is equivalent to or higher than the inhibitory effect when the acid site is masked with alkali metal. Although the detailed mechanism is not elucidated at present, it is presumed that a sulfur element forms a complex oxide with alumina, thereby altering the configuration of the acid site, which remains in the case of using alumina alone, to a different configuration. The form obtained when a sulfur element forms a complex oxide with alumina is presumably generally in a sulfate group form. The sulfate group itself is acidic and the number of acid sites, i.e., acidity, presumably increases by the existence thereof. However, it is estimated that these acid sites do not contribute to progress of the decomposition reaction at a relatively low reaction temperature.

From the above, the present invention can provide a metal catalyst which eliminates the necessity of masking the acid site with alkali metal. In general, it is preferable, in terms of performances of the catalyst, to mask the acid site with alkali metal by impregnating and loading active metals such as noble metals, and further impregnating the same according to the amount of the acid site which remains after the first impregnation and loading. However, repeating the impregnating processes, drying, and calcining increases the cost for industrially manufacturing a catalyst. Therefore, in the case of a catalyst not requiring the masking with alkali metal, the cost for the masking can be reduced. A sulfur compound can be incorporated in a carrier by various methods as described above. For example, a sulfur compound can be incorporated in a range suitable for an alumina carrier by using a sulfur compound in a process of manufacturing an alumina carrier, and since the sulfur compound is generally inexpensive, it is possible to manufacture a carrier containing sulfur with little effect on the manufacturing cost of an alumina carrier. Therefore, the catalyst manufacturing cost is generally inexpensive as compared with the case where masking with alkali metal is carried out.

In the present invention, when catalyst metal is loaded on a catalyst carrier, the above-mentioned catalyst carrier may be impregnated with a solution of the above-mentioned catalyst metal, dried, and calcined at a predetermined temperature. As a solution of catalyst metal compound, chloride, bromide, ammonium salt, carbonyl compound, of various complex compounds, an amine complex, an ammine complex, an acetylacetonato complex, of the catalyst metal can be mentioned. For example, when the catalyst metal is platinum, platinum compounds such as chloroplatinic acid, platinum acetylacetonate, ammonium platinate, bromo platinate, platinum dichloride, platinum tetrachloride hydrate, platinum carbonyl dichloride, and dinitro diamine platinate are mentioned.

For example, when preparing a dehydrogenation catalyst in which the catalyst carrier is the above-mentioned porous γ-alumina carrier and the catalyst metal is platinum: the porous γ-alumina carrier is impregnated with a solution of the above-mentioned platinum compound; the resultant is dried preferably at 50° C. or higher and 200° C. or lower for 0.5 hour or more and 48 hours or less; the resultant is calcined preferably at 350° C. or higher and 600° C. or lower for 0.5 hour or more and 48 hours or less, and more preferably at 350° C. or higher and 450° C. or lower for 0.5 hour or more and 5 hours or less; and the resultant is subjected to hydrogen reduction treatment in an hydrogen gas atmosphere under reduction conditions at 350° C. or higher and 600° C. or lower for 0.5 hour or more and 48 hours or less, and preferably 350° C. or higher and 550° C. or lower for 3 hours or more and 24 hours or less. When the temperature at the time of the hydrogen reduction is less than 350° C., there is a problem that platinum is not fully reduced, while when the temperature at the time of the hydrogen reduction exceeds 600° C., there is a problem that sintering of platinum particles occurs at the time of reduction, and the metal dispersion degree decreases.

In the uniformly, highly dispersed metal catalyst of the present invention, catalyst metal is loaded not only on the surface of a catalyst carrier but also over the entire cross section of the catalyst carrier, and since the loading amount of the catalyst metal can be increased while maintaining such a high dispersion ratio, the catalytic activity is improved. For example, when platinum as catalyst metal is loaded on a porous γ-alumina carrier as a catalyst carrier, platinum can be loaded in a dispersion ratio as high as 50% or higher until the loading amount of platinum reaches about 2% by weight. For example, the uniformly, highly dispersed metal catalyst of the present invention can be preferably used as: dehydrogenation catalysts for monocyclic hydrogenated aromatics such as cyclohexane, methylcyclohexane, and dimethylcyclohexane; bicyclic hydrogenated aromatics such as tetralin, decalin, and methyldecalin; and tricyclic hydrogenated aromatics such as tetradecahydroanthracene, which are used as a hydrogen storage for use in a hydrogen supply system according to, for example, a chemical hydride method.

A sulfur-containing porous metal oxide in which sulfur or a sulfur compound serving as a carrier of the uniformly, highly dispersed metal catalyst of the present invention is substantially uniformly dispersed throughout the cross section of the carrier can be applied not only to a catalyst carrier but also to adsorbent and the like. Since sulfur exists over the entire carrier, metal ion and the like can be rapidly adsorbed as far as the inside of an adsorbent, the uniformly, highly dispersed metal catalyst of the present invention is useful also as an adsorbent for use in recovering metal ion and the like.

Effect of the Invention

In the uniformly, highly dispersed metal catalyst of the present invention, the catalyst metal is loaded on the catalyst carrier in a state where the catalyst metal is dispersed throughout the cross section of the catalyst carrier, therefore, the loading amount of the catalyst metal increases, and excellent performances in terms of catalytic activity, selectivity, life, etc., are exhibited.

Moreover, according to the method of producing the uniformly, highly dispersed metal catalyst of the present invention, a uniformly, highly dispersed metal catalyst in which the catalyst metal is loaded on the catalyst carrier in a state where the catalyst metal is dispersed throughout the cross section of the catalyst carrier can be easily produced.

BEST MODE FOR CARRYING OUT THE INVENTION

Figure 1:
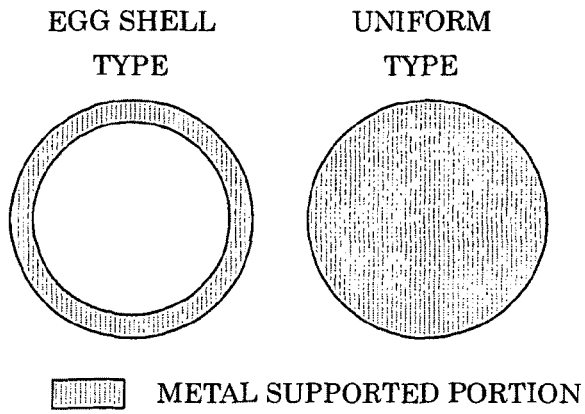
FIG. 1 illustrates carrier states of each of an egg shell-type catalyst and a uniform-type catalyst according to the classification of metal-loaded state as viewed from the catalyst cross section of metal-loaded catalysts.

First, the metal-loaded state of each of an egg shell-type catalyst and a uniform-type catalyst of the present invention will be described with reference to FIG. 1. The egg shell-type refers to a state where a metal member to be loaded is dispersed and loaded only on the outer shell part of one cross section of a formed catalyst. The uniform-type refers to a state where a metal member is dispersed throughout the cross section and a metal member is loaded over the entire inside of a formed catalyst.

Hereinafter, preferable embodiments of the present invention will be specifically described based on Examples and Comparative Example.

Comparative Example 3,900 cc of aqueous aluminum nitrate solution with a concentration of 2.67 mol/L was prepared and simultaneously, 3,900 cc of 14% aqueous ammonia solution was prepared. 20 L of pure water was placed in a 30-L enamel container, and the container was warmed to 70° C. under stirring. While continuing stirring, a pH swing operation in which 1,300 cc of aqueous aluminum nitrate solution was placed, followed by stirring for 5 minutes (pH2.0), and thereafter, 1,300 cc of aqueous ammonia solution was placed, followed by stirring for 5 minutes (pH 7.4) was performed 4 times. An aqueous slurry solution of the obtained aluminum hydroxide was filtered to recover a cake, subjecting the cake to a washing operation in which the cake was re-dispersed in 20 L of pure water, followed by filtering again was performed 3 times, obtaining a washed gel.

The washed cake was air dried to adjust the moisture, and then was formed into a rod-like shape having a diameter of 1.6 mm with an extruder. The resultant was dried (120° C., 3 hours), crushed to about 1 cm in length, baked in a muffle furnace (500° C., 3 hours), thereby yielding an alumina carrier A containing no sulfur.

Figure 2:
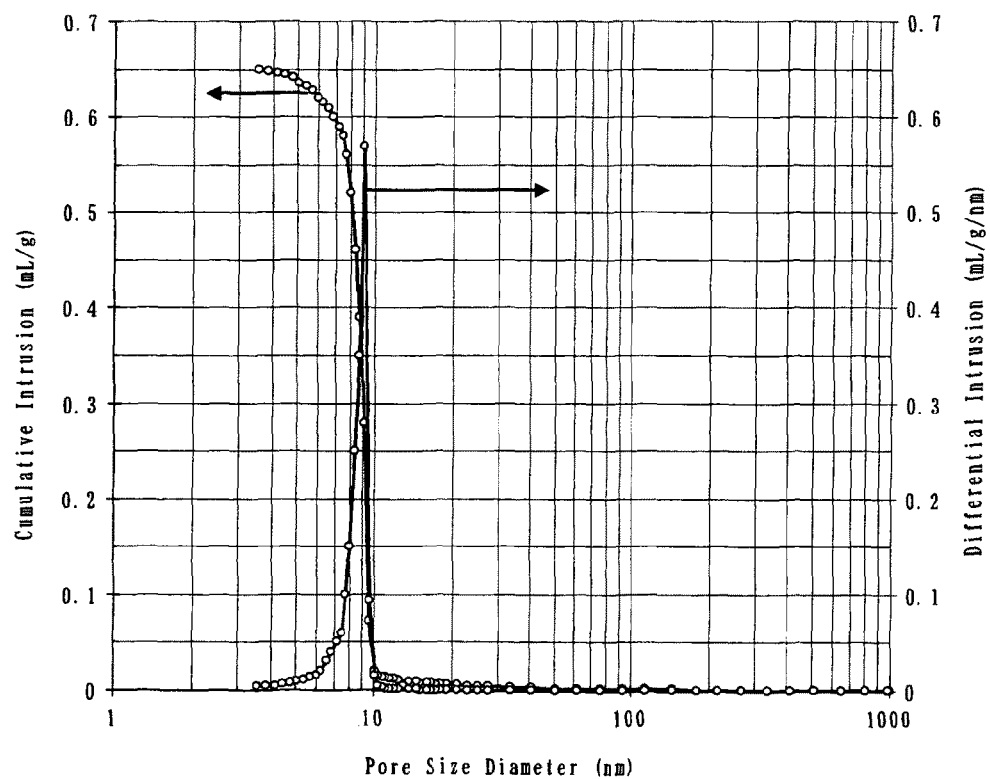
FIG. 2 is a view illustrating a pore distribution measured by a mercury porosimetry of a carrier A according to Comparative Example of the present invention.

The alumina carrier A thus obtained had a BET surface area of 275 m$^2$/g, a pore volume of 0.65 cm$^3$/g, and an average pore size of 8.9 nm, which were determined by a mercury porosimetry, and had a sharp pore distribution in which the pore sizes of almost all of the pores were concentrated near the average pore size. In addition, the volume occupied by pores having a diameter of 7 to 10 nm was 80% or more of the total pore volume. The pore distribution of the carrier A is shown in FIG. 2.

The alumina carrier A thus prepared was impregnated with an aqueous chloroplatinic acid solution whose pH was adjusted to 2.0 so that the platinum-loaded amount after calcination was 0.6% by weight. Thereafter, moisture was removed with an evaporator, and the resultant was dried (at 120° C. for 3 hours) and calcined (at 400° C. for 3 hours). Then, the resultant was placed in a flow-type hydrogen-reducing apparatus, and hydrogen reduction was carried out at 450° C. for 15 hours in a hydrogen stream, thereby yielding a 0.6 wt % platinum-loaded alumina catalyst No. 1.

Figure 3:
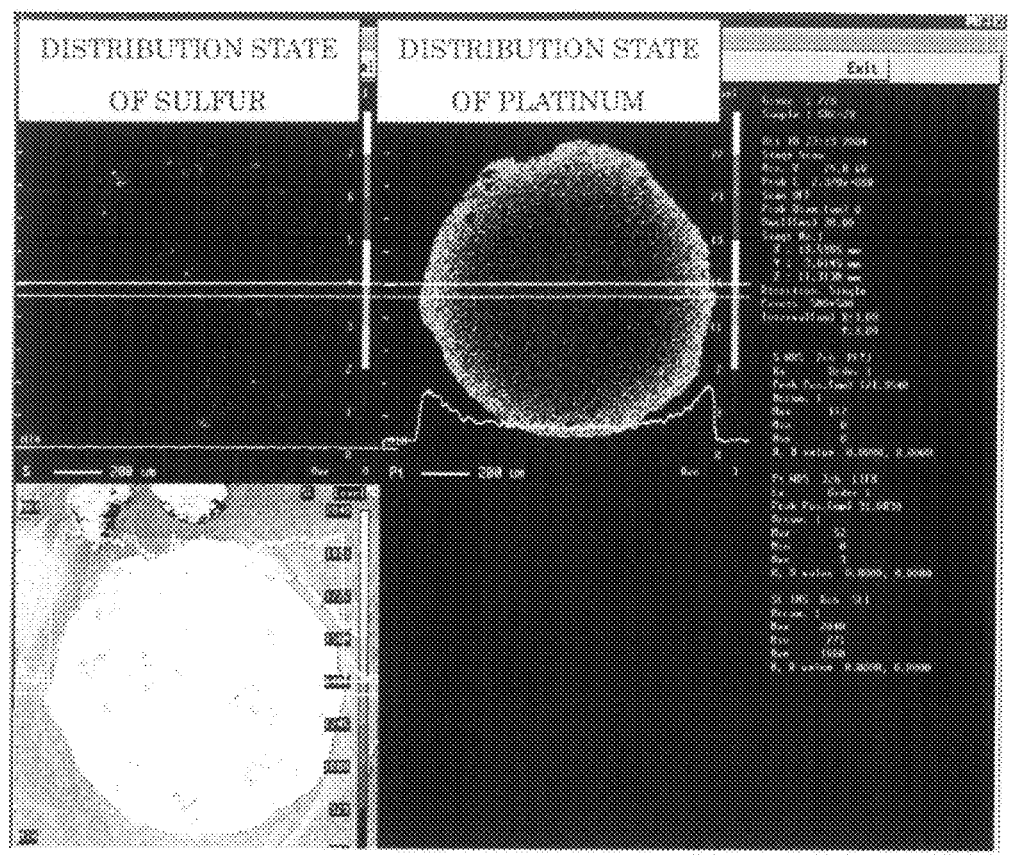
FIG. 3 is distribution measurement diagrams of a sulfur element and a platinum element measured by EPMA with respect to a 0.6 wt % platinum-loaded alumina catalyst (catalyst No. 1) using a carrier A according to Comparative Example 1 of the present invention.

With respect to the obtained catalyst No. 1, the concentrations of sulfur element and platinum element on the catalyst cross section were quantified by surface analysis and line analysis using EPMA (Electron probe micro analyzer; JXA-8900R manufactured by JEOL Co., Ltd.). The results are shown in FIG. 3. As is clear from the results shown in FIG. 3, it is revealed that, in the catalyst prepared using the carrier containing no sulfur, the platinum elements are dispersed and loaded on the outer shell part of the cross section.

Example 1

The pH swing operation was performed 3 times in the same manner as in the preparation of the alumina carrier A, and washing was similarly performed, yielding a washed gel. Sulfur powder was added to the gel so that the sulfur powder was 0.5% by weight with respect to the weight of alumina after calcination, and uniformly kneaded. Thereafter, the resultant was formed, dried, and calcined in the same manner as in the case of the carrier A, yielding an alumina carrier B containing the sulfur powder. It should be noted that when adding the sulfur powder to the washed gel, the powder was not kneaded in the cake. The sulfur powder was added under stirring to the gel in the form of high concentration slurry in which the cake was dispersed in pure water, followed by filtration, yielding an alumina carrier C containing the sulfur powder from a gel obtained by sufficiently kneading the cake with a kneader in the same manner as in the carrier B.

Each of the alumina carriers B and C thus prepared was impregnated with an aqueous chloroplatinic acid solution whose pH was adjusted to 2.0 so that the platinum-loaded amount after calcination was 0.6% by weight. Thereafter, moisture was removed with an evaporator, and the resultants were dried (at 120° C. for 3 hours) and calcined (at 400° C. for 3 hours). Then, the resultants were placed in a flow-type hydrogen-reducing apparatus, and hydrogen reduction was carried but at 450° C. for 15 hours in a hydrogen stream, thereby yielding 0.6 wt % platinum-loaded alumina catalysts No. 2 and No. 3.

Figure 4:
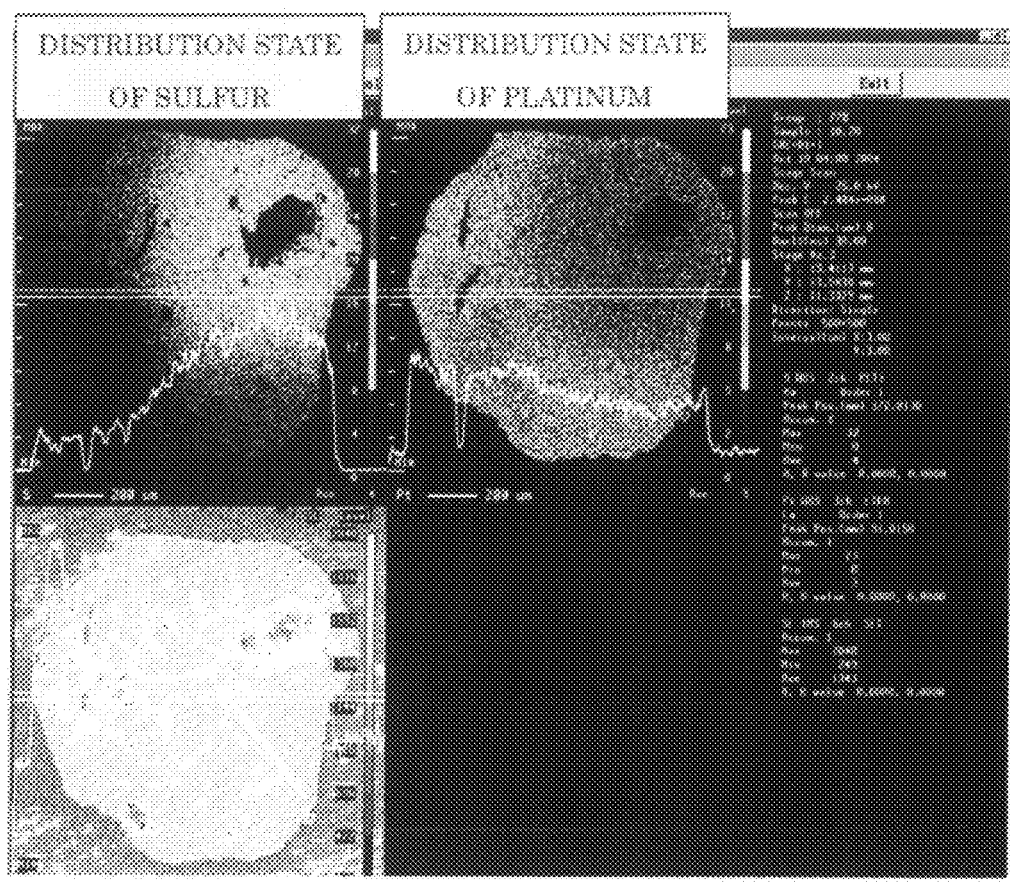
FIG. 4 is distribution measurement diagrams of a sulfur element and a platinum element measured by EPMA with respect to a 0.6 wt % platinum-loaded alumina catalyst (catalyst No. 2) using a carrier B according to Example 1 of the present invention.

With respect to the obtained catalysts No. 2 and No. 3, the concentrations of sulfur elements and platinum elements on the catalyst cross section were quantified by surface analysis and line analysis using EPMA. The results are shown in FIG. 4 (catalyst No. 2) and FIG. 5 (catalyst No. 3). As is clear from the results shown in FIG. 4 (catalyst No. 2), it is revealed that the platinum elements are substantially uniformly dispersed in a portion where the sulfur is moderately dispersed, and the platinum elements are successfully dispersed not only on the outer shell part but also over the entire inside of the catalyst cross section in the alumina carrier in which the sulfur powder is kneaded. However, in the carrier in which the sulfur powder is directly kneaded in the cake, since the sulfur powder is difficult to sufficiently disperse, the sulfur powder is locally concentrated, and no platinum is dispersed in such a portion. Thus, it is revealed that an excessively high sulfur concentration is not suitable for dispersing platinum.

Figure 5:
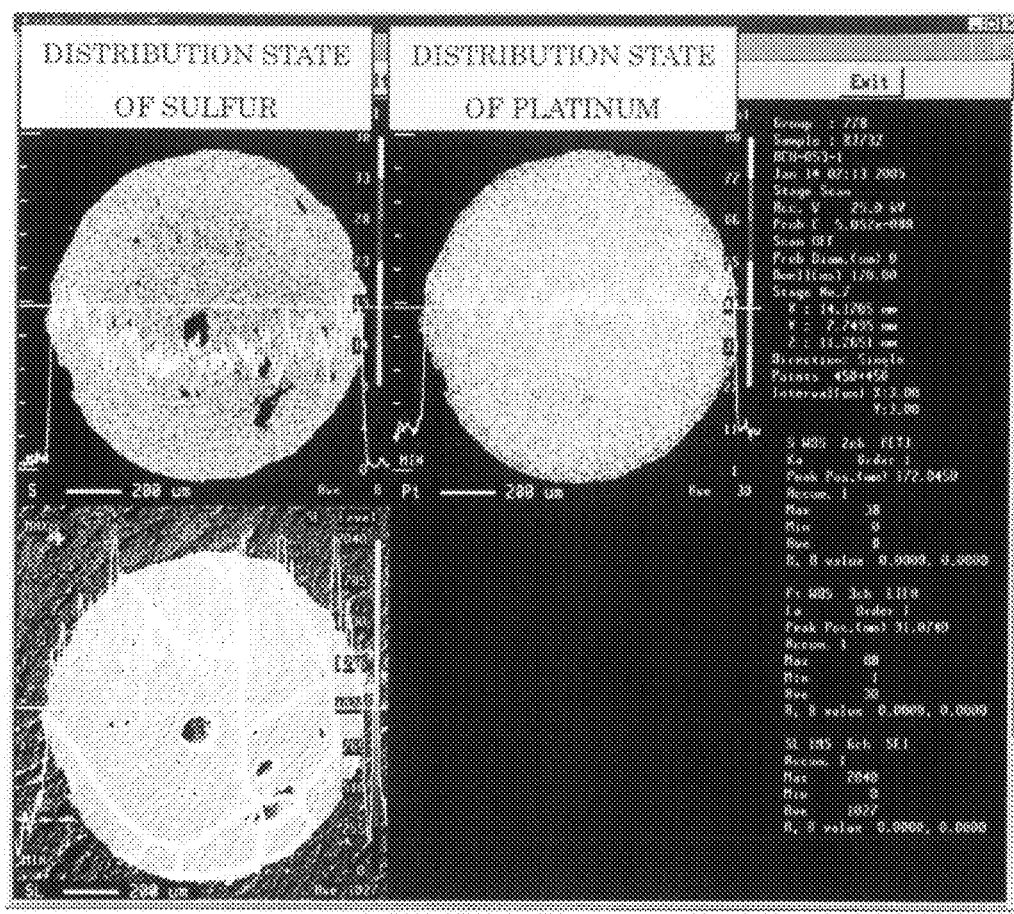
FIG. 5 is distribution measurement diagrams of a sulfur element and a platinum element measured by EPMA with respect to a 0.6 wt % platinum-loaded alumina catalyst (catalyst No. 3) using a carrier C according to Example 1 of the present invention.

In contrast, as is clear from the results shown in FIG. 5 (catalyst No. 3), it is revealed that the sulfur powder that is added to the cake in the form of a high concentration slurry is sufficiently dispersed, and, in the catalyst No. 3 prepared from such a carrier, both the sulfur elements and the platinum elements are substantially uniformly dispersed throughout the carrier, and the distribution pattern of the platinum elements is substantially in agreement with the distribution pattern of the sulfur elements.

Example 2

3,900 cc of aqueous aluminum sulfate solution with a concentration of 0.9 mol/L was prepared and simultaneously, 3,900 cc of 14% aqueous ammonia solution was prepared. 7 L of pure water was placed in a 10 L enamel container, and the container was warmed to 70° C. under stirring. While continuing stirring, a pH swing operation in which 400 cc of aqueous aluminum sulfate solution was placed, followed by stirring for 5 minutes (pH 2.0), and thereafter, 300 cc of aqueous ammonia solution was placed, followed by stirring for 5 minutes (pH 7.4) was performed 3 times. An aqueous slurry solution of the obtained aluminum hydroxide was filtered to recover a cake, subjecting the cake to a washing operation in which the cake was re-dispersed in 7 L of pure water, followed by filtering again was performed twice, obtaining a washed gel.

The washed cake was air dried to adjust the moisture, and then was formed into a rod-like shape having a diameter of 1.6 mm with an extruder. The resultant was dried (120° C., 3 hours), crushed to about 1 cm in length, calcined in a muffle furnace (500° C., 3 hours), thereby yielding an alumina carrier D containing sulfur. At this time, the sulfur content remaining in the carrier D was about 0.5%.

Figure 6:
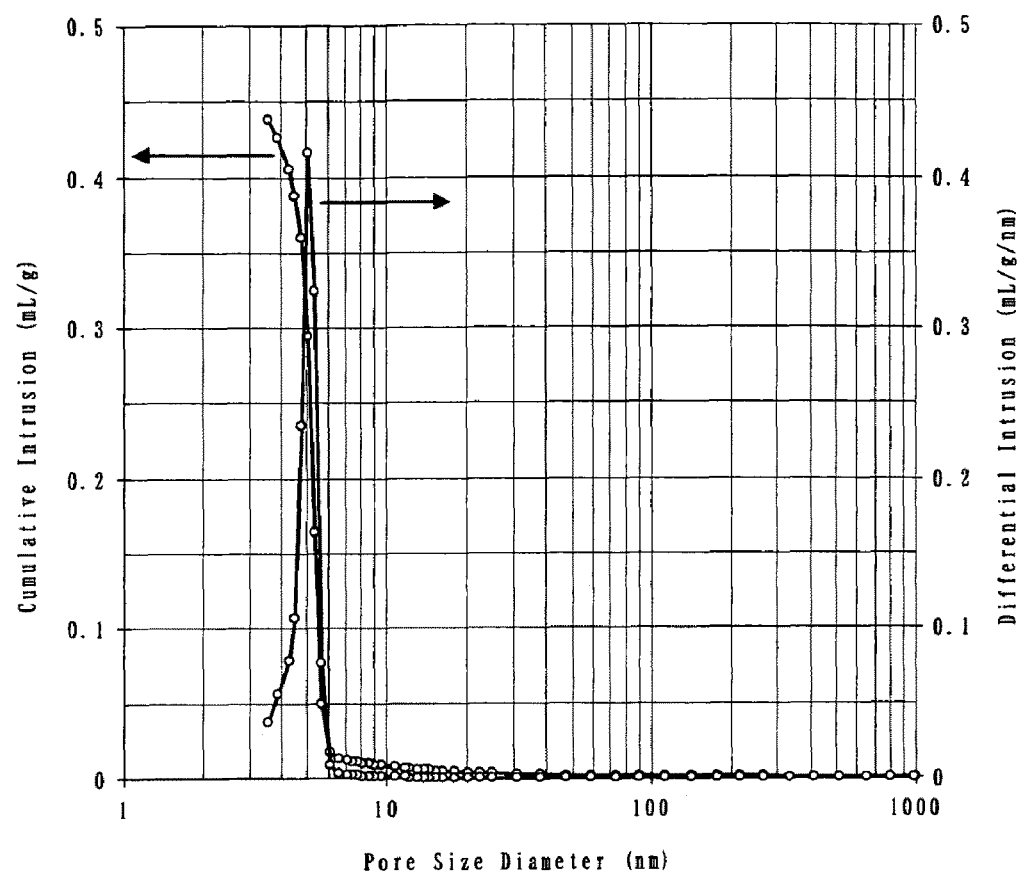
FIG. 6 is a view illustrating a pore distribution measured by a mercury porosimetry of a carrier D according to Example 2 of the present invention.

The alumina carrier D thus obtained had a BET surface area of 300 m$^2$/g, a pore volume of 0.46 cm$^3$/g, and an average pore size of 5.6 nm, which were determined by a mercury porosimetry, and had a sharp pore distribution in which the pore sizes of almost all of the pores were concentrated near the average pore size. In addition, the volume occupied by pores having a diameter of 4 to 6 nm was 80% or more of the total pore volume. The pore distribution of the carrier D is shown in FIG. 6.

The alumina carrier D thus prepared was impregnated with an aqueous chloroplatinic acid solution whose pH was adjusted to 2.0 so that the platinum-loaded amount after calcination was 0.6% by weight. Thereafter, moisture was removed with an evaporator, and the resultant was dried (at 120° C. for 3 hours) and calcined (at 400° C. for 3 hours). Then, the resultant was placed in a flow-type hydrogen-reducing apparatus, and hydrogen reduction was carried out at 450° C. for 15 hours in a hydrogen stream, thereby yielding a 0.6 wt % platinum-loaded alumina catalyst No. 4.

With respect to the obtained catalysts No. 4, the concentrations of sulfur element and platinum element on the catalyst cross section were quantified by surface analysis and line analysis using EPMA. The results are shown in FIG. 7.

Figure 7:
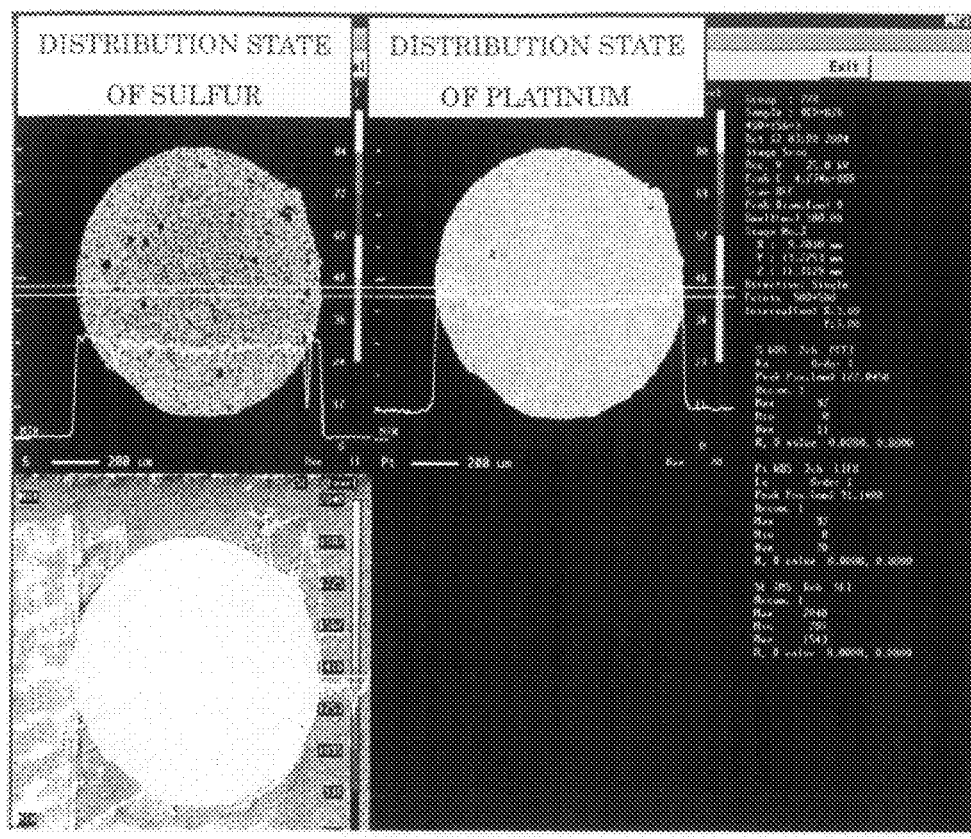
FIG. 7 is distribution measurement diagrams of a sulfur element and a platinum element measured by EPMA with respect to a 0.6 wt % platinum-loaded alumina catalyst (catalyst No. 4) using the carrier D according to Example 2 of the present invention.

As is clear from the results shown in FIG. 7, it is revealed that both the sulfur elements and the platinum elements are substantially uniformly dispersed throughout the carrier also in a catalyst prepared using an alumina carrier in which sulfur is incorporated by synthesizing the carrier using sulfate for an alumina source, and removing excessive sulfate groups by washing in the preparation process of the alumina carrier and that the distribution pattern of the platinum elements are substantially in agreement with the distribution pattern of the sulfur elements.

Example 3

Supports A containing no sulfur were impregnated with an aqueous ammonium sulfate solution with a concentration of 0.38 mol/L so that the sulfur content after calcination of the resultants were 0.1% by weight, 0.5% by weight, or 1.2% by weight, respectively, and then, each solvent was removed with an evaporator. The resultants were dried (120° C., 3 hours), and calcined (500° C., 3 hours), thereby yielding an alumina carrier E (0.1% by weight), an alumina carrier F (0.5% by weight), and an alumina carrier G (1.2% by weight) each containing sulfur.

Each of the alumina carriers E and F thus prepared was impregnated with an aqueous chloroplatinic acid solution whose pH was adjusted to 2.0 so that the platinum loading amount after calcination was 0.6% by weight. Thereafter, moisture was removed with an evaporator, and the resultants were dried (at 120° C. for 3 hours) and calcined (at 400° C. for 3 hours). Then, the resultants were placed in a flow-type hydrogen-reducing apparatus, and hydrogen reduction was carried out at 450° C. for 15 hours in a hydrogen stream, thereby yielding a 0.6 wt % platinum-loaded alumina catalysts No. 5, No. 6, and No. 7. With respect to the obtained catalysts No. 5, No. 6, and No. 7, the concentrations of sulfur element and platinum element on each of the catalyst cross sections were quantified by surface analysis and line analysis using EPMA. The results are shown in FIG. 8 (catalyst No. 5), FIG. 9 (catalyst No. 6), and FIG. 10 (catalyst No. 7).

Figure 8:
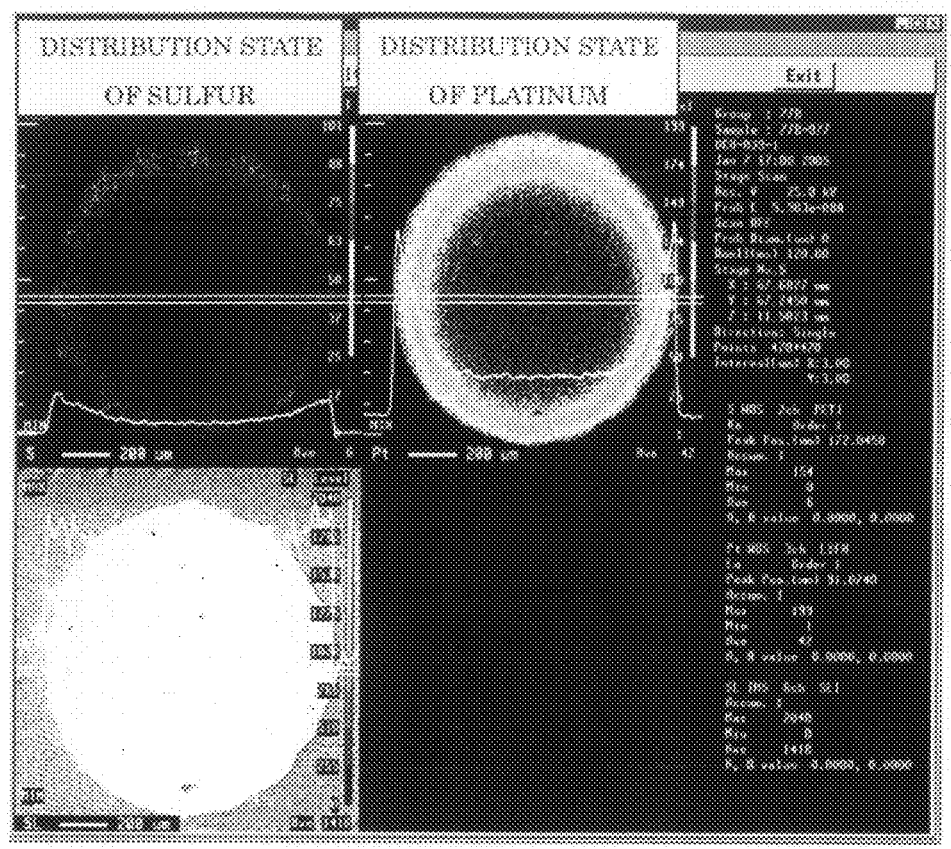
FIG. 8 is distribution measurement diagrams of a sulfur element and a platinum element measured by EPMA with respect to a 0.6 wt % platinum-loaded alumina catalyst (catalyst No. 5) using a carrier E according to Example 3 of the present invention.

As is clear from the results shown in FIG. 8 (catalyst No. 5), it is revealed that when the content of the sulfur element in a catalyst is about 0.1% by weight, the sulfur itself is difficult to uniformly disperse in the catalyst, and when the sulfur content is about 0.1% by weight, the dispersion of sulfur is insufficient. When platinum is loaded using such a carrier, platinum is dispersed in a relatively thick outer shell part where sulfur exists, and platinum is not loaded inside a catalyst in which sulfur does not exist, resulting in an egg shell-type catalyst. A carrier which has low sulfur content does not allow uniform dispersion. However, it is revealed that the thickness of the outer shell part of the egg shell type in which platinum is dispersed and loaded can be controlled utilizing the fact.

Figure 9:
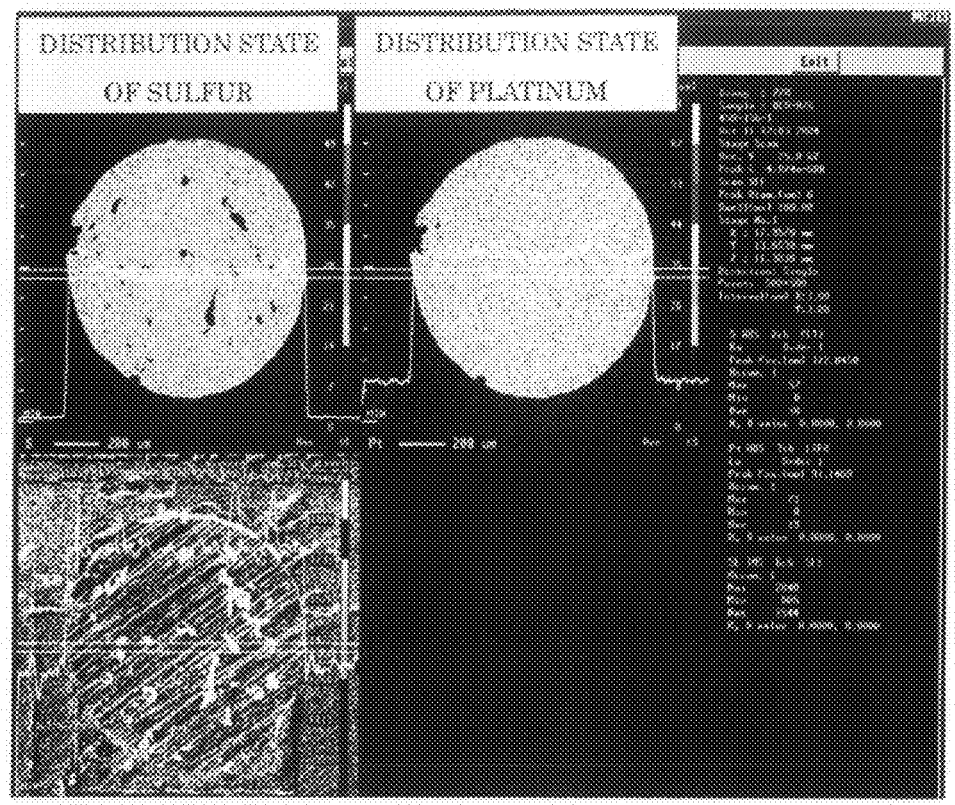
FIG. 9 is distribution measurement diagrams of a sulfur element and a platinum element measured by EPMA with respect to a 0.6 wt % platinum-loaded alumina catalyst (catalyst No. 6) using a carrier F according to Example 3 of the present invention.

As is clear from the results shown in FIG. 9 (catalyst No. 6), it is revealed that, in the catalyst, when the content of the sulfur element is 0.5% by weight, the sulfur itself is uniformly dispersed in the catalyst, both the sulfur elements and the platinum elements are substantially uniformly dispersed throughout the carrier, and the distribution pattern of the platinum elements is substantially in agreement with the distribution pattern of the sulfur elements.

Figure 10:
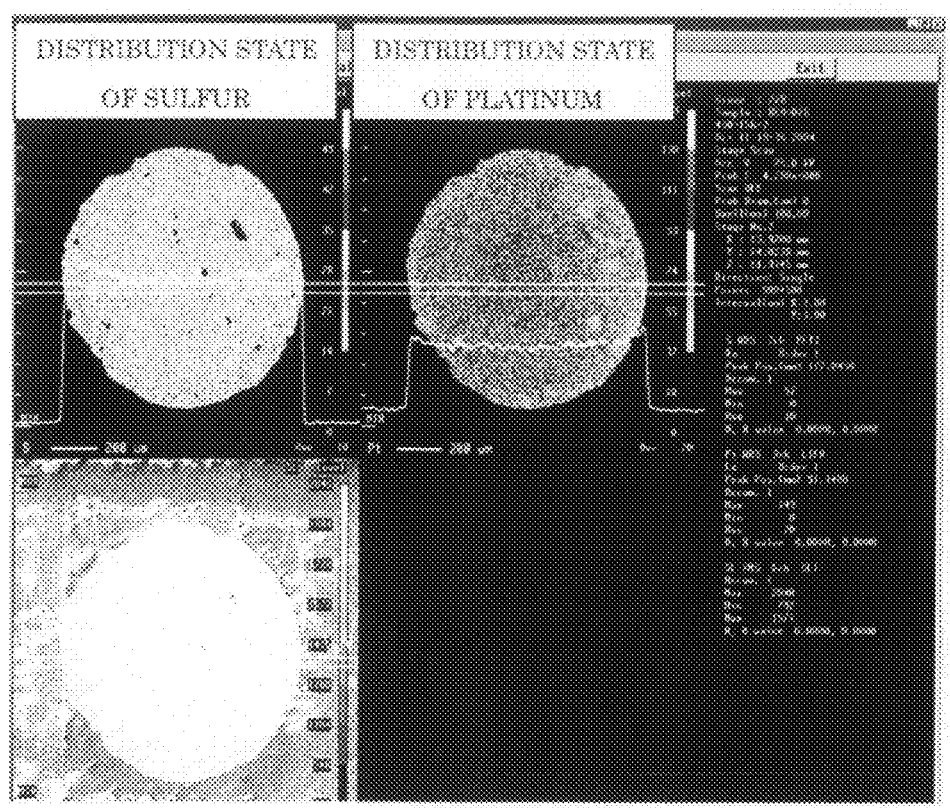
FIG. 10 is distribution measurement diagrams of a sulfur element and a platinum element measured by EPMA with respect to a 0.6 wt % platinum-loaded alumina catalyst (catalyst No. 7) using a carrier G according to Example 3 of the present invention.

As is clear from the results shown in FIG. 10 (catalyst No. 7), it is revealed that, in the catalyst, when the content of the sulfur element is 1.2% by weight, the sulfur itself is uniformly dispersed in the catalyst, both the sulfur elements and the platinum elements are substantially uniformly dispersed throughout the carrier, and the distribution pattern of the platinum elements is substantially in agreement with the distribution pattern of the sulfur elements.

Example 4

The dispersion ratio of platinum of each of the catalysts No. 1 to No. 7 prepared in Comparative Example and Examples 1 to 3 above was measured by a CO pulse adsorption method.

The CO pulse adsorption method will be described below. When CO is pulsatively injected into a catalyst sample, the CO is adsorbed on the surface of loaded metal and the amount of eluted CO is small in the early stage of the injection. After a while, the CO is adsorbed on almost the entire surface of the loaded metal, and almost all of the injected CO is eluted in a steady state. At this time, the amount of eluted CO at the time of the first adsorption is subtracted from the amount of eluted CO in the steady state, and the sum of the differences is defined as the CO adsorption amount. The CO pulse adsorption method refers to a method for calculating a metal surface area, dispersion ratio, and particle diameter from the adsorption amount and the loaded metal content. The calculation method is specifically described below.

The adsorption gas amount V per g of catalyst at 0° C. was calculated from the CO gas amount Vt in which a sample amount of catalyst W(g) was adsorbed at a measurement temperature according to the following equation (1).

$$V = (Vt/W) \times \{273/(273+t)\} \text{ (ml/g·cat)} \quad (1)$$

Here, when the metal content of the sample is defined as C (%) and the atomic weight of the loaded metal is defined as M, the number of moles R of the loaded metal per g of the sample is calculated according to the following equation (2).

$$R = (C/100) \times (1/M) \text{ (mol/g·cat)} \quad (2)$$

The number of moles K of the adsorption gas amount per g of the sample is calculated according to the following equation (3).

$$K = V/(22.4 \times 10^{-3} \times 10^6) \text{ (mol/g·cat)} \quad (3)$$

Based on the above, the dispersion ratio B (proportion of effective surface metal in the loaded metal) is calculated according to the following equation (4).

$$B = (K/R) \times 100(\%) \quad (4)$$

When the lattice constant of the loaded metal catalyst is defined as a (Å), and it is assumed that one adsorption gas molecule is adsorbed to a lattice constant area $a^2$, the specific surface area S of metal is calculated according to the following equation.

$$S = \text{the number of gas molecules adsorbed to 1 g of sample} \times a^2 = K \times 6.02 \times 10^{23} \times (a \times 10^{-10})^2 \quad (5)$$

When a loaded metal particle is assumed to be a cube D (m) on each side, five surfaces out of six surfaces of the particle are effective. Based on the fact, the following equations are established.

$$\text{Effective area } S \text{ of one particle} = 5D^2 \text{ (m}^2\text{)} \quad (6)$$

$$\text{Volume of one particle } v = D^3 \text{ (m}^3\text{)} \quad (7)$$

When the number of particles of the loaded metal per g of sample is defined as n, the following equations are established.

$$\text{Specific surface area } S \text{ of loaded metal} = ns = n5D^2 \text{ (m}^2\text{)} \quad (8)$$

$$\text{Volume } Vc \text{ of loaded metal} = nv = Nd^3 \text{ (m}^3\text{)} \quad (9)$$

From equations (10 to 11) and equations (10 to 12), $$S/Vc = 5/D \therefore D = 5Vc/S(m) \quad (10)$$

When the content of loaded metal is defined as C (%) and the specific gravity is defined as d(g/cm$^3$), the volume Vc of the loaded metal per g of sample is calculated according to the following equations.

$$Vc = \text{loaded metal weight (g/g) per g of sample/Specific gravity of loaded metal (g/cm}^3\text{)} = C/100/d \text{ (g/cm}^3\text{)} \quad (11)$$

$$\text{Particle diameter} = 5Vc/S$$
$$= \{5(C/100/d) \times 10^{-6}\}/S(m)$$
$$= \{5(C/100/d) \times 10^{-6} \times 10^{10}\}/S(\text{Å}).$$

The measurement results of the dispersion ratio of platinum measured by the CO pulse adsorption method in the catalysts No. 1 to No. 7 prepared in Comparative Example and Examples 1 to 3 above are shown in the following Table 1 (dispersion ratio and particle diameter measured by the CO pulse adsorption method).

TABLE 1

| Catalyst No. | Support (%) | Sulfur content (wt %) | Platinum-loading amount (wt %) | Dispersion ratio (%) | Particle diameter (Å) |
|---|---|---|---|---|---|
| 1 | A | 0 | 0.6 | 69 | 7.1 |
| 2 | B | 0.5 | 0.6 | 46 | 11 |
| 3 | C | 0.5 | 0.6 | 68 | 7.2 |
| 4 | D | 0.5 | 0.6 | 74 | 6.7 |
| 5 | E | 0.1 | 0.6 | 67 | 7.4 |
| 6 | F | 0.5 | 0.6 | 76 | 6.5 |
| 7 | G | 1.2 | 0.6 | 71 | 6.9 |

Example 5

A carrier A containing no sulfur and a carrier D containing sulfur were impregnated with an aqueous ammonium rhodium hexachloride solution for 50 hours, and then the solvents were removed with an evaporator. The resultants were dried (at 120° C. for 3 hours), thereby and calcined (at 400° C. for 3 hours), thereby yielding a 0.6 wt % rhodium-loaded alumina catalysts. The concentrations of sulfur element and platinum element on each of the catalyst cross sections were quantified by surface analysis and line analysis using EPMA. The results are shown in FIG. 11.

Figure 11:
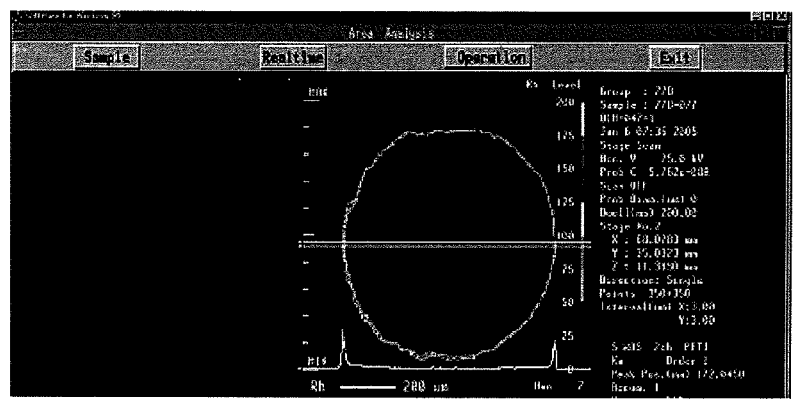
FIG. 11 are distribution measurement diagrams of a sulfur element and a platinum element measured by EPMA with respect to each 0.6 wt % rhodium-loaded alumina catalyst (catalyst No. 8) prepared using the carrier A containing no sulfur according to Comparative Example of the present invention and the carrier D containing sulfur according to Example 2 of the present invention.
Figure 11:
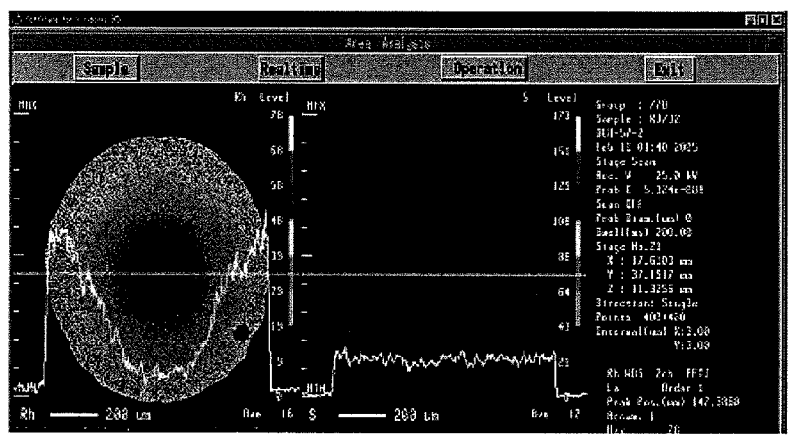

As is clear from the results shown in FIG. 11, when the carrier A containing no sulfur was used, an egg shell-type catalyst is obtained in which rhodium (Rh) is loaded only on the outer shell part of the catalyst cross section. In contrast, it is revealed that a catalyst prepared from the carrier D containing sulfur is an egg shell type-catalyst, but the outer shell part is thick and rhodium is dispersed as far as the center. This shows that, by reducing the diameter of a compact of an alumina carrier, a rhodium-loaded alumina catalyst in which rhodium is substantially uniformly dispersed as far as the center can be prepared.

Example 6

Among the 0.6% by weight platinum-loaded alumina catalysts obtained in each Example above, the dehydrogenation reaction test of methylcyclohexane (MCH) was carried out for the catalyst No. 3 (Example 1), catalyst No. 4 (Example 2), catalyst No. 6 (Example 3), catalyst No. 7 (Example 3), and catalyst No. 1 (Comparative Example). 10 cc of each catalyst above was placed in a stainless steel reaction tube whose inside diameter is 12.6 mm$\phi \times$300 mm and which is equipped with a protective tube for a thermocouple whose outer dimension was ⅛ inch in the center of the cross section of the reaction tube in such a manner that the center of a catalyst bed was positioned in the longitudinal center of the reaction tube, and 10 cc of α-alumina beads with a diameter of 1 mm$\phi$ was placed on the upper side of the catalyst as a preheating layer. The temperature of the catalyst bed was increased in a hydrogen stream (LHSV=5.0; 50 cc/hr) so that the central temperature of the catalyst bed reached 320° C. Subsequently, methylcyclohexane (MCH) in an amount equivalent to LHSV=2.0 (20 cc/hr) was supplied to a reactor with a liquid-supply pump for high speed liquid chromatography (HPLC) (HPLC pump). Immediately, a hydrogen flow rate was adjusted so that the hydrogen gas amount was adjusted to 5 mol % with respect to the total amount of MCH and hydrogen gas. The reaction test was performed while adjusting the output of an electric furnace so that the central temperature of a catalyst bed was 320° C. during the reaction.

A vapor-liquid separator was placed at the outlet of the reaction tube, and the resultant was separated into a liquid reaction product such as toluene and gas such as hydrogen gas, which were generated by the dehydrogenation reaction. The collected liquid product and gas were separately analyzed by gas chromatography.

The MCH conversion rate (%), toluene selectivity (%), toluene yield (%), and hydrogen generation amount (cc/h/cc-cat) 2 hours after and 300 hours after the initiation of the reaction were calculated. The results are shown in Table 2.

The dehydrogenation reaction test of methylcyclohexane was carried out for the catalyst No. 3 (Example 1), catalyst No. 4 (Example 2), catalyst No. 6 (Example 3), catalyst No. 7 (Example 3), and catalyst No. 1 (Comparative Example) prepared in Comparative Example and Examples 1 to 3 above. The results are shown in Table 2.

TABLE 2

| | Catalyst No. | | | | |
|---|---|---|---|---|---|
| | 1 | 3 | 4 | 6 | 7 |
| Support | A | C | D | F | G |
| Sulfur content (wt %) | 0 | 0.5 | 0.5 | 0.5 | 1.2 |
| Platinum-loading amount (wt %) | 0.6 | 0.6 | 0.6 | 0.6 | 0.6 |

TABLE 2-continued

| | Catalyst No. | | | | |
|---|---|---|---|---|---|
| | 1 | 3 | 4 | 6 | 7 |
| 24 hours after the initiation of reaction | | | | | |
| MCH conversion (%) | 98.2 | 98.0 | 98.0 | 98.2 | 97.9 |
| Toluene selectivity (%) | 99.88 | 99.97 | 99.94 | 99.92 | 99.95 |
| Toluene yield (%) | 98.1 | 98.0 | 97.9 | 98.1 | 97.9 |
| Concentration of generated methane (ppm) | 180 | 70 | 55 | 50 | 45 |
| 300 hours after the initiation of reaction | | | | | |
| MCH conversion (%) | 94.5 | 97.83 | 97.68 | 97.7 | 97.4 |
| Toluene selectivity (%) | 99.9 | 99.97 | 99.93 | 99.93 | 99.97 |
| Toluene yield (%) | 94.4 | 97.8 | 97.6 | 97.6 | 97.4 |
| Concentration of generated methane (ppm) | 115 | 55 | 40 | 35 | 30 |

As is clear from the results shown in Table 2, it is revealed that the dehydrogenated catalyst of the present invention shows notably high selectivity and markedly low concentration of methane, which is generated by a side reaction, compared with a catalyst prepared from an alumina carrier containing no-sulfur, even if the acid site is not masked using alkali metal such as potassium. Moreover, considering that stable performances are maintained over 300 hours and deactivation in catalyst performances is not observed, hydrogen can be stably generated with favorable selectivity over a long period of time.

INDUSTRIAL APPLICABILITY

In the uniformly, highly dispersed metal catalyst of the present invention, catalyst metal is loaded on a catalyst carrier in a state where the catalyst metal is uniformly dispersed throughout the catalyst carrier. Therefore, the loading amount of the catalyst metal increases and excellent performances are exhibited in terms of catalytic activity, selectivity, life, etc. Thus, the uniformly, highly dispersed metal catalyst of the present invention is suitably used as a dehydrogenation catalyst for a hydrogen storage for use in a chemical hydride hydrogen supply system and the like, and suitably used for manufacturing chemical products, producing hydrogen, cleaning the environment, such as cleaning of exhaust gas. Moreover, according to the production method for the uniformly, highly dispersed metal catalyst of the present invention, such a uniformly, highly dispersed metal catalyst can be readily manufactured industrially.

The invention claimed is:

1. An uniformly, highly dispersed metal catalyst, comprising:
   a catalyst carrier made of a metal oxide; and
   a catalyst metal having catalytic activity,
   the catalyst metal being loaded on the catalyst carrier, wherein:
   the catalyst carrier is a sulfur-containing catalyst carrier which comprises an aluminum carrier having a surface area of 150 m²/g or larger, a fine pore volume of 0.4 cm³/g or larger, an average fine pore diameter of 40 to 300 Å, and the proportion of fine pores having an average fine pore diameter of 30 Å is 60% or higher with respect to a total pore volume and sulfur or a sulfur compound which is dispersed throughout a cross section of the aluminum carrier and whose content is 0.15 to 3.0% by weight in terms of a sulfur element; and
   in the sulfur-containing catalyst carrier, platinum or rhodium is dispersed and loaded as the catalyst metal over an entire cross section of the catalyst carrier substantially in agreement with distribution of the sulfur or the sulfur compound.

2. An uniformly, highly dispersed metal catalyst according to claim 1, wherein the sulfur or the sulfur compound is one or two or more members selected from sulfur (S), sulfuric acid, a sulfate, and an organosulfur compound.

3. An uniformly, highly dispersed metal catalyst according to claim 1, wherein a loading amount of the catalyst metal is 0.1 to 3.0% by weight in terms of catalyst metal (Me).

4. An uniformly, highly dispersed metal catalyst according to claim 1, wherein the sulfur-containing catalyst carrier is a compact or powder comprising a sulfur-containing porous γ-alumina carrier.

5. An uniformly, highly dispersed metal catalyst according to claim 1, wherein the catalyst metal is dispersed on the sulfur-containing catalyst carrier in a dispersion ratio of 40% or more measured by a CO pulse adsorption method.

6. A method of dehydrogenating a hydrogenated aromatic, comprising dehydrogenating hydrogenated aromatic using the uniformly, highly dispersed metal catalyst according to any one of claim 1, 2, 3, 4, or 5.

7. A method of dehydrogenating a hydrogenated aromatic according to claim 6, wherein the hydrogenated aromatic is one member or a mixture of two or more members selected from a hydride of monocyclic aromatic, a hydride of bicyclic aromatic, and a hydride of compound having three or more aromatic rings.

8. A method of producing an uniformly, highly dispersed metal catalyst, comprising:
   kneading sulfur powder in an aluminum gel serving as a precursor of an alumina;
   forming the resulting gel into a predetermined shape, followed by drying and calcining to prepare a sulfur-containing catalyst carrier in which sulfur or a sulfur compound is dispersed throughout a cross section thereof;
   impregnating the obtained sulfur-containing catalyst carrier with an aqueous solution of catalyst metal compound of platinum and/or rhodium;
   drying the resulting catalyst carrier to obtain a dried matter loading the catalyst metal compound;
   reducing the dried matter loading the catalyst metal compound as it is in a hydrogen atmosphere; or calcining the obtained dried matter loading the catalyst metal compound to obtain a calcined matter loading catalyst metal; and
   reducing the obtained calcined matter loading the catalyst metal with hydrogen.

9. A method of producing the uniformly, highly dispersed metal catalyst according to claim 8, comprising, at the time of impregnating the sulfur-containing catalyst carrier with a solution of catalyst metal compound, adjusting a pH value of the impregnation solution within a range of 1.8 to 3.0.

10. A method of producing the uniformly, highly dispersed metal catalyst according to claim 8 or 9, wherein the sulfur-containing catalyst carrier is a sulfur-containing porous γ-alumina carrier.

11. A method of producing the uniformly, highly dispersed metal catalyst according to claim 10, wherein the sulfur-containing porous γ-alumina carrier has a surface area of 150 m²/g or more, a fine pore volume of 0.40 cm³/g, an average fine pore diameter of 40 to 300 Å, and fine pores with the average fine pore diameter of ±30 Å occupying 60% or more of a total fine pore volume.

12. A method of producing the uniformly, highly dispersed metal catalyst according to claim 10, wherein the sulfur-containing catalyst is prepared at a calcination temperature of 350 to 800° C. for a calcination time of 1.0 to 24 hours.

* * * * *